United States Patent [19]

DeBoer

[11] Patent Number: 4,654,431

[45] Date of Patent: Mar. 31, 1987

[54] PHOTOPOLYMERIZABLE THIOACRYLATE MONOMERS

[75] Inventor: Charles D. DeBoer, Rochester, N.Y.

[73] Assignee: Eastman Kodak Company, Rochester, N.Y.

[21] Appl. No.: 416,766

[22] Filed: Sep. 10, 1982

Related U.S. Application Data

[63] Continuation-in-part of Ser. No. 238,403, Feb. 26, 1981, abandoned.

[51] Int. Cl.$^4$ ............... C07D 265/30; C07D 333/56; C07D 307/02; C07D 319/12
[52] U.S. Cl. .................................. 558/257; 549/58; 549/499; 549/378; 548/562; 548/572; 548/342; 548/125; 548/379; 548/249; 548/214; 548/247; 546/203; 546/205; 546/173; 526/286; 558/252; 558/256; 544/158
[58] Field of Search ............ 260/455 R, 239 B; 549/79, 499, 427, 346, 13, 9; 548/572; 546/195; 558/252, 256, 257

[56] References Cited

PUBLICATIONS

Otsu, Chem. Abs., vol. 70, 1969, 29348a.

Primary Examiner—Henry R. Jiles
Assistant Examiner—Robert C. Whittenbaugh
Attorney, Agent, or Firm—William J. Davis

[57] ABSTRACT

A novel photocurable monomer having the formula:

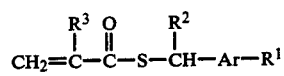

wherein:
Ar is arylene;
$R^1$ is H, alkyl, alkoxy, amino, halogen, sulfide, sulfoxide, sulfonate, aryl or heterocyclic;
$R^2$ is H, alkyl, aryl or aralkyl; and
$R^3$ is H or methyl, is useful in preparing a polymer having a high refractive index. The polymer is useful in optical components, such as lenses.

2 Claims, No Drawings

PHOTOPOLYMERIZABLE THIOACRYLATE MONOMERS

This is a continuation-in-part application of Ser. No. 238,403 filed on Feb. 26, 1981 now abandoned.

BACKGROUND OF THE INVENTION

1. Field of the Invention

This invention relates to novel thioacrylate monomers, polymers of thioacrylates and optical components containing these polymers.

2. Description Relative to the Prior Art

Optical components, such as lenses, prisms, and light guides, are known in the art. It is necessary that materials used for making optical components be colorless and transparent. It is also desirable that these materials have a high refractive index. In the case of lenses, the use of high refractive index materials makes possible the use of thinner lenses having the same focal length as thicker lenses made of materials with a lower refractive index. The use of thinner lenses decreases the volume of space required by the lens within an optical assembly. Also, the manufacture of thinner lenses requires less material, which constitutes a potential savings to the manufacturer.

High refractive index materials have also been shown to be desirable in light guides. U.S. Pat. No. 3,809,686, issued Mar. 19, 1970, describes the method of producing light guides by selectively irradiating polymethyl methacrylate with ultraviolet light at given wavelengths. The selective irradiation causes observable increases in the refractive index of the polymer along the path of the focused radiation. However, the index of refraction of polymethyl methacrylate is only 1.49 to 1.50 and the increases produced by irradiation are relatively small. (The resulting change is refractive index equals $0.5 \times 10^{-6} E$, where E is the exposure in joules per square centimeter for ultraviolet light from a mercury arc.) The use of polymers having a substantially higher refractive index (over 1.60) in optical components would make possible the use of optical components which are considerably thinner than conventionally prepared components. It is thus seen that transparent and colorless polymers of high refractive indices are desirable for use in optical components.

SUMMARY OF THE INVENTION

Polymers of high refractive index are prepared by photopolymerizing a monomer having the formula:

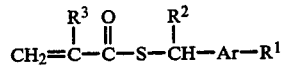

wherein:
Ar is arylene;
$R^1$ is H, alkyl, alkoxy, amino, halogen, sulfide, sulfoxide, sulfonate, aryl or heterocyclic;
$R^2$ is H, alkyl, aryl or aralkyl; and
$R^3$ is H or methyl.

The resulting polymer comprises from 5 to 100 percent of the above monomer and from 0 to 95 percent of a copolymerizable ethylenically unsaturated monomer. The polymer is substantially colorless and transparent and has a refractive index over 1.60. The high refractive index renders the resulting polymer particularly useful in optical components, such as lenses.

DETAILED DESCRIPTION OF PREFERRED EMBODIMENTS

The novel monomer is represented by the formula:

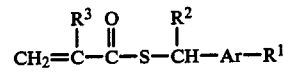

wherein:
Ar is arylene, preferably containing from about 6 to about 22 carbon atoms, such as phenylene, naphthylene, anthracene, perylene, acenaphthene or rubrene;

$R^1$ is H; alkyl, preferably containing from about 1 to about 20 carbon atoms, such as methyl, ethyl, isopropyl or hexyl; alkoxy, preferably containing from about 1 to about 20 carbon atoms, such as methoxy or ethoxy; amino; halogen such as chloride or bromide; sulfide; sulfoxide; sulfonate; aryl, preferably containing from about 6 to about 18 carbon atoms, such as phenyl; or heterocyclic, preferably a 5 to 7-membered ring which may be saturated, such as pyrrolidine, morpholine, piperidine, tetrahydrofurane, dioxane or quinaldine, or unsaturated, such as pyrrole, isoxazole, imidazole, isothiazole, furazan or pyrazoline. Such heterocyclic rings contain S, N or O as the heteroatom.

$R^2$ is H, alkyl as described for $R^1$, aryl as described for $R^1$ or aralkyl such as benzyl. When $R^2$ is aralkyl it contains at least 7 carbon atoms and, as is the case with aryl, up to about 18 carbon atoms $R^3$ is H or methyl.

It is noted that substituted alkyl, aryl and arylene, such as methoxy ethyl, chlorophenyl and bromonaphthyl are useful herein.

Examples of monomers useful herein include:

(1) S-(1-naphthylcarbinyl)thioacrylate

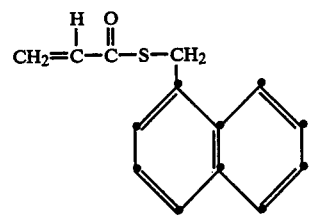

(2) S-(2-naphthylcarbinyl)thioacrylate

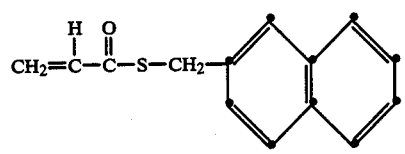

(3) S-(1-naphthylcarbinyl)thiomethacrylate

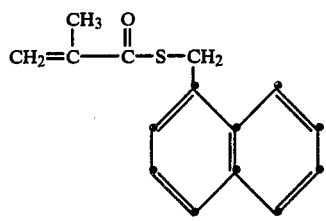

(4) S-(1-naphthylethyl)thioacrylate

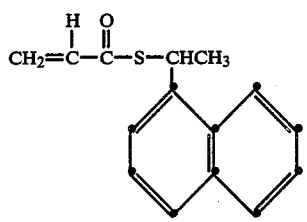

(5) 1-bromo-2-naphthyl methylthioacrylate

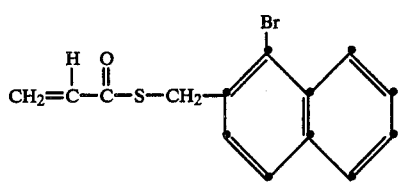

(6) S-(2-naphthylcarbinyl)thiomethacrylate

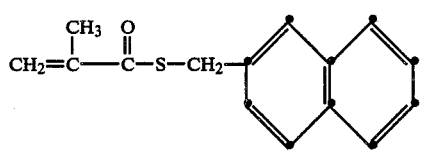

(7) S-(1-naphthylethyl)thiomethacrylate

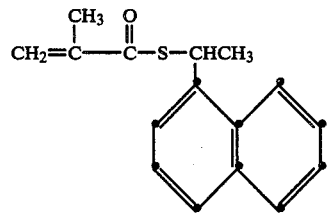

(8) 1-bromo-2-naphthyl methyl thiomethacrylate

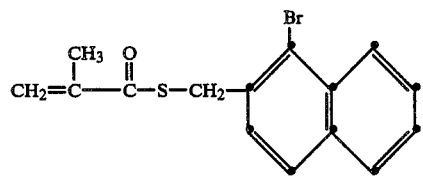

(9) S-(3-benzo-[b]thienyl)methyl thioacrylate

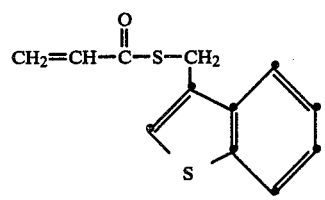

(10) S-(3-benzo-[b]thienyl)methyl thiomethylacrylate

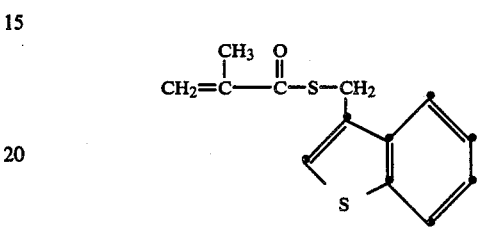

(11) S-(2,4-dichloro)benzyl thioacrylate

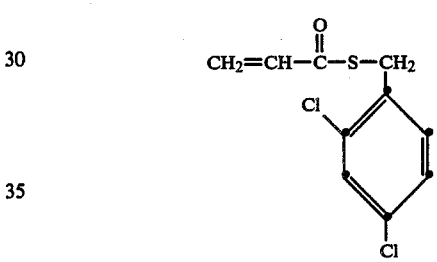

(12) S-(2,4-dichloro)benzyl thiomethacrylate

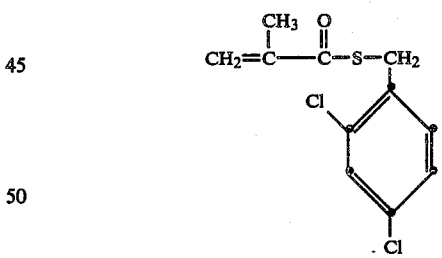

(13) S-[1-(2-methylnaphthyl)]methyl thioacrylate

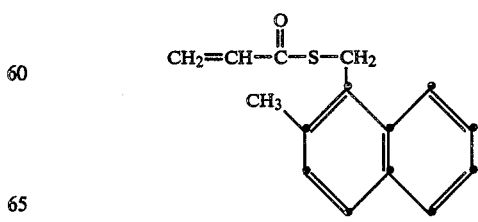

(14) [1-(2-methylnaphthyl)]methyl thiomethacrylate

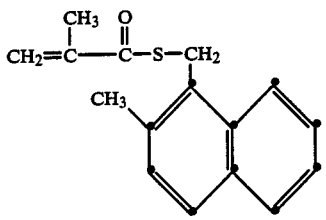

(15) S-5-(acenaphthenyl)methyl thioacrylate

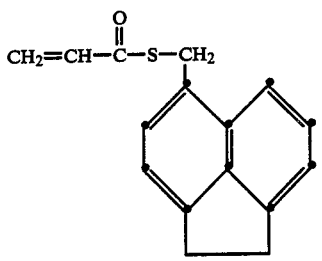

(16) S-5-(acenaphthenyl)methyl thiomethacrylate

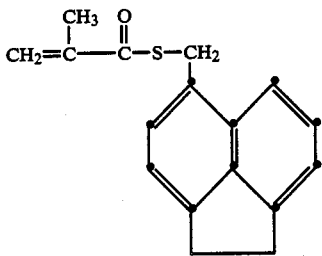

Other useful monomers include 1-dimethylamino-2-naphthyl thioacrylate, 1-dimethylamino-2-naphthyl thiomethacrylate, 1-methoxy-2-naphthyl thioacrylate, 1-methoxy-2-naphthyl thiomethacrylate, 1-phenyl-2-naphthyl thioacrylate, 1-phenyl-2-naphthyl thiomethacrylate, 1-morpholino-2-naphthyl thioacrylate, 1-morpholino-2-naphthyl thiomethacrylate, S-(3-benzo[b]thienyl)phenylmethyl thioacrylate and S-(3-benzo[b]thienyl)phenylmethyl thiomethacrylate.

The preferred monomers have the structures:

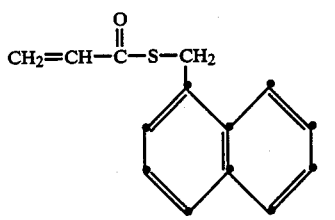

(1)

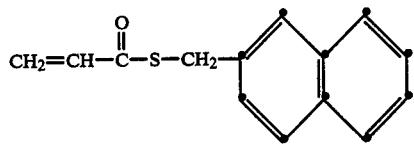

(2)

-continued

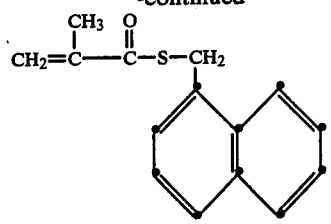

(3)

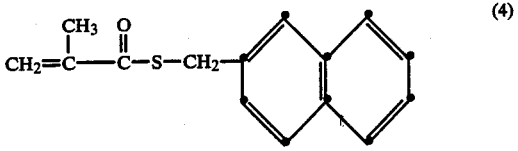

(4)

The monomers of the present invention are prepared by heating the appropriate mercaptan, such as 1-(naphthylcarbinyl)mercaptan with a 0-20% molar excess of bicycloheptene carbonyl chloride in an organic solvent, such as methylene chloride, at a temperature of 30°-50° C., while an acid-accepting amine, such as diisopropylethylamine is slowly added to the mixture. The product is distilled under conditions favorable to the splitting off of cyclopentadiene, such as vacuum distillation at 200°-300° C., resulting in a good yield of the monomers such as S-(1-naphthylcarbinyl)thioacrylate.

The starting material, bicycloheptene carbonyl chloride, is prepared by stirring cyclopentadiene with a 0-20% molar excess of acryloyl chloride and an organic solvent, such as methylene chloride, at a reduced temperature, such as −70° to −85° C., and allowing the mixture to warm slowly to room temperature. The acid chloride product is isolated by distillation.

The monomer of the present invention has a melting point less than or equal to 50° C. Monomers having melting points over 50° C. form bubbles or exhibit nonuniform crystallization when polymerized in situ. Bubbles or crystals in the resulting polymers scatter light and cause loss of image sharpness in the optical components in which they are used.

The polymer of this invention is one having:

(a) from 5 to 100 mole percent of recurring units having the formula:

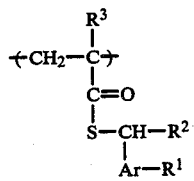

where Ar, $R^1$, $R^2$ and $R^3$ are described above; and (b) from 0 to 95 mole percent of a polymerized copolymerizable ethylenically unsaturated monomer.

Examples of copolymerizable ethylenically unsaturated monomers useful herein include alkyl acrylates and methacrylates such as methyl acrylate, ethyl acrylate, propyl acrylate, butyl acrylate, and butyl methacrylate; vinyl esters, amides, nitriles, ketones, halides, ethers, olefins and diolefins, as exemplified by acrylonitrile, methacrylonitrile, styrene, α-methyl styrene, acrylamide, methacrylamide, vinyl chloride, methyl vinyl ketone, fumaric, maleic and itaconic esters, 2-chloroethylvinyl ether, dimethylaminoethyl methacrylate, 2- hydroxyethyl methacrylate, N-vinylsuccinamide, N-vinylphthalimide, N-vinylpyrrolidone, butadiene and ethylene.

Preferred monomers which are useful herein include acrylates and methacrylates. A most preferred monomer is benzyl methacrylate.

The novel polymer can be prepared by adding a small amount of photoinitiator (0.001–1.0 weight percent) such as benzoin methyl ether to the novel monomer or a mixture of preferably 50 to 100 mole percent of the novel monomer and 0–50% of a copolymerizable ethylenically unsaturated monomer described above. The mixture can be polymerized at a temperature of 20°–30° C. by irradiation with a near-ultraviolet lamp. The resulting polymer has an index of refraction above 1.60, typically in the range from 1.60 to 1.70. The use of polymers having a refractive index over 1.60 in optical components permits the use of components which are considerably thinner than conventionally prepared components. Other methods of polymerization can similarly be used. Such methods can include thermal polymerization, polymerization by electron beam irradiation and polymerization by high energy gamma irradiation. Examples of the polymers of the invention include:

poly[S-(1-naphthylcarbinyl)thioacrylate];
poly[S-(2-naphthylcarbinyl)thioacrylate];
poly[S-(1-naphthylcarbinyl)thioacrylate-co-benzyl methacrylate];
poly[S-(2-naphthylcarbinyl)thioacrylate-co-benzyl methacrylate];
poly[S-(1-naphthylcarbinyl)thiomethacrylate];
poly[S-(2-naphthylcarbinyl)thiomethacrylate];
poly[S-(1-naphthylcarbinyl)thiomethacrylate-co-benzyl methacrylate]; and
poly[S-(2-naphthylcarbinyl)thiomethacrylate-co-benzyl methacrylate].

The novel polymers of this invention are useful in optical components. The term "optical component" is defined as that portion of an optical assembly having as its function the refraction of light. As used herein, the term "optical component" refers to materials which can also reflect, diffract and transmit light. However, "optical components" is directed preferably toward components in which changes in refractive capability affect the overall utility of the component. "Refraction," as used herein, is defined as the deflection from a straight path undergone by a light ray or energy wave in passing obliquely from one medium (as air) into another (as glass or other optical material) in which its velocity is different. The term "optical assembly" as used herein is defined as a collection of manufactured parts in a complete machine, structure, or unit of a machine relating to the scientific study or use of electromagnetic radiation. The term "optical components" includes refractive materials, such as lenses, lens adhesives, prisms, mirrors, solid light pipes, light guides, fiber optics, phase-retardation plates and twistels.

The term "prism" as used herein is defined as a transparent body bounded in part by two plane faces that are not parallel, said body being used to deviate or disperse a beam of light. Prisms can be used in telescopes, binoculars, beam splitters, rangefinders, spectroscopes, spectrographs, spectrophotometers, refractometers and anamorphic systems.

A "mirror" is defined as a polished or smooth surface (as glass) that forms images by reflection. Mirrors can be used in telescopes, beam splitters, range-finders, reflecting microscope objectives and condensing systems.

A "solid light pipe" is defined as a transparent body tapered to form a cone used to internally reflect a meridional ray incident on the untapered end of the cone from the conical wall at progressively lower angles of incidence until it is delivered to the tapered end of the cone, as described in Smith, *Modern Optical Engineering*, 1966, chapter 9. Light pipes can be used to enlarge the field of view of a radiometer with a small detector.

A "light guide" is defined as a transparent body having substantially tubular pathways of higher-refractive index material encased by a lower-refractive index material used to internally reflect a meridional ray incident on the entrance end from the walls of the tubular pathways at substantially equal angles of incidence until it is delivered to the exit end of the guide, as described in U.S. Pat. No. 3,809,686. Light guides can be used in electronics to couple simple circuits optically and without capacitative effects.

"Fiber optics" are defined as transparent bodies in the form of long polished cylinders in which light strikes the walls of the cylinder with an angle of incidence greater than the critical angle for total internal reflection used to transmit light from one end to another without substantial leakage, either as a single fiber or bound together in flexible bundles of fibers as disclosed by Smith, *Modern Optical Engineering*, 1966, chapter 9. Fiber optics are used in medical diagnostic instruments such as flexible gastroscopes, in fire detectors to relay signals to a sensor located behind a heat shield, in data-processing equipment to sense holes in punched cards or marks on examination forms, and in photometers and colorimeters to serve as flexible probes for a fixed sensor.

A "phase retardation plate" is defined as a transparent body used to produce phase shifts in incident radiation resulting in elliptically or circularly polarized light. Phase retardation plates may be a pair of movable biaxial crystals in the form of wedges having perpendicularly aligned optical axes, such as Babinet compensators, Soleil compensators and the like. Or the desired phase shifts may be produced by total internal reflection in a phase retardation plate, such as a Fresnel rhomb. Various phase retardation plates are described by Kingslake, *Applied Optics and Optical Engineering*, 1965, volume I, chapter 9. Phase retardation plates are used in ellipsometers to study reflectance characteristics of metals and properties of surface films of liquids with polarized light.

In a particularly preferred embodiment of this invention, the monomers and polymers are useful as materials for making lenses. A "lens" is a transparent body having two opposite regular surfaces, either both curved or one curved and the other plane, and which is used either singly or combined in an optical instrument for forming an image by focusing rays of light. It has been found that, because of the higher refractive index of these polymers, it is possible to produce lenses which are thinner than lenses made with polymers having refractive indices under 1.60, e.g., polymethylmethacrylate, n=1.49 to 1.50.

The lenses of this invention are not only thinner than conventionally prepared lenses, but require less curvature, occupy a smaller volume of space and thus provide more freedom in assembly of multi-element lenses than prior art lenses. They also require less polymer to produce, constituting a potential cost savings to the manufacturer.

Monomers of this invention are useful in producing optical components by polymerization in situ. Thus, the resulting polymer forms the final material of which the optical component is comprised.

In a preferred embodiment, a lens is prepared from the novel polymer in the following manner. A mixture of from 5 to 100 mole percent of a preferred monomer, such as S-(1-naphthylcarbinyl)thioacrylate, from 0 to 95 mole percent of a copolymerizable ethylenically unsaturated monomer, such as benzyl methacrylate, and a small amount of photoinitiator is prepared. A preferred molar ratio for the mixture is about 84/16 S-(1-naphthylcarbinyl)thioacrylate:benzyl methacrylate. A mold of the desired shape, such as a concave glass lens is filled with the mixture and covered with a sheet of plate glass. The assembly is polymerized by irradiation of near-ultraviolet light. The resulting lens is clear and transparent and contains the polymer of this invention having a refractive index over 1.60.

The following examples are included for a further understanding of the invention.

EXAMPLE 1

A mixture of 66 g of cyclopentadiene and 500 ml of methylene chloride was stirred with 90 g of acryloyl chloride at dry ice temperature ($-78.5°$ C.) and allowed to warm slowly to room temperature over 24 hours. The reaction product was then distilled. The resulting bicycloheptene carbonyl chloride thus obtained was allowed to react with 1-(naphthylcarbinyl)-mercaptan and refluxed in methylene chloride (b.p. $40°-41°$ C.) while one equivalent of diisopropylethylamine was slowly added to the mixture. The product was vacuum distilled, using a 250° C. oil bath, under which conditions the cyclopentadiene split off, giving S-(1-naphthylcarbinyl)thioacrylate in good yield. A thin-layer chromatograph (50:50 hexane/ether, silica gel) of the resulting monomer indicated as $R_f$ value of 0.69 to 0.72. An infrared spectrum made of the resulting monomer showed the following bands: 1677 cm$^{-1}$(s), 1620 cm$^{-1}$(m), 1519 cm$^{-1}$(w), 1400 cm$^{-1}$(s), 1175 cm$^{-1}$(m), 1014 cm$^{-1}$(s), and 780 cm$^{-1}$(s). A nuclear magnetic resonacne spectrum of the resulting monomer showed a complex multiplet at 7.58 (7H), a doublet at 6.28 (2H), a triplet at 5.48 (1H) and a singlet at 4.58 (2H).

EXAMPLE 2

A mixture of 34 g of S-(1-naphthylcarbinyl)thioacrylate, 5 g of benzyl methacrylate, and 0.2 g of benzoin methyl ether photoinitiator, and 0.3 g of aerosol OT mold release, a product of American Cyanamid having the formula:

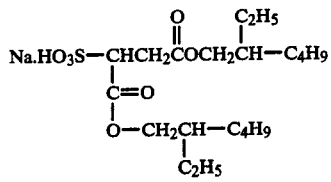

was prepared. A concave glass lens, used as a mold, was filled with the mixture and covered with a sheet of 0.30-inch thick plate glass. The assembly was polymerized at a distance of four inches from a 15-watt, near-ultraviolet Blak-light for one hour at room temperature. The resulting lens was clear and transparent.

The invention has been described in detail with particular reference to certain preferred embodiments thereof, but it will be understood that variations and modifications can be effected within the spirit and scope of the invention.

I claim:

1. A monomer having the formula:

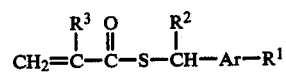

wherein Ar is naphthylene, $R^1$ is H, $R^2$ is H, and $R^3$ is H or methyl.

2. A monomer selected from the group consisting of:
S-(1-naphthylcarbinyl)thioacrylate,
S-(2-naphthylcarbinyl)thioacrylate,
S-(1-naphthylcarbinyl)thiomethacrylate,
S-(1-naphthylethyl)thioacrylate,
1-bromo-2-naphthyl methylthioacrylate,
S-(2-naphthylcarbinyl)thiomethacrylate,
S-(1-naphthylethyl)thiomethacrylate,
1-bromo-2-naphthyl methyl thiomethacrylate,
S-(3-benzo-[b]thienyl)methyl thioacrylate,
S-(3-benzo-[b]thienyl)methyl thiomethacrylate,
S-[1-(2-methylnaphthyl)]methyl thioacrylate,
S-[1-(2-methylnaphthyl)]methyl thiomethacrylate,
S-5-(acenaphthenyl)methyl thioacrylate,
S-5-(acenaphthenyl)methyl thiomethacrylate,
1-dimethylamino-2-naphthyl thioacrylate,
1-dimethylamino-2-naphthyl thiomethacrylate,
1-methoxy-2-naphthyl thioacrylate,
1-methoxy-2-naphthyl thiomethacrylate,
1-phenyl-2-naphthyl thioacrylate,
1-phenyl-2-naphthyl thiomethacrylate,
1-morpholino-2-naphthyl thioacrylate,
1-morpholino-2-naphthyl thiomethacrylate,
S-(3-benzo-[b]thienyl)phenylmethyl thioacrylate, and
S-(3-benzo-[b]thienyl)phenylmethyl thiomethacrylate.

* * * * *